United States Patent [19]
Yamaguchi et al.

[11] Patent Number: 4,927,448
[45] **Date of Patent: * May 22, 1990**

[54] THIADIAZABICYCLONONANE DERIVATIVES AND HERBICIDAL COMPOSITIONS

[75] Inventors: Mikio Yamaguchi; Chiharu Suzuki, both of Shizuoka; Kenji Matsunari, Fujieda; Takeshige Miyazawa, Shizuoka; Yasuo Nakamura, Tokyo, all of Japan

[73] Assignees: Kumiai Chemical Industry Co., Ltd.; Ihara Chemical Industry Co., Ltd., both of Tokyo, Japan

[ * ] Notice: The portion of the term of this patent subsequent to Dec. 5, 2006 has been disclaimed.

[21] Appl. No.: 257,805

[22] Filed: Oct. 14, 1988

[30] Foreign Application Priority Data

Oct. 16, 1987 [JP] Japan ............................... 62-260866

[51] Int. Cl.[5] .................... C07D 513/04; A01N 43/82
[52] U.S. Cl. ......................................... 71/90; 544/235
[58] Field of Search ............................. 544/235; 71/90

[56] References Cited

U.S. PATENT DOCUMENTS

| | | | |
|---|---|---|---|
| 4,272,281 | 6/1981 | Quadranti | 71/90 |
| 4,420,327 | 12/1983 | Jikihara et al. | 71/90 |
| 4,482,373 | 11/1984 | Handte | 71/90 |
| 4,536,209 | 8/1985 | Jikihara et al. | 71/90 |
| 4,816,063 | 3/1989 | Yamaguchi et al. | 544/235 |

FOREIGN PATENT DOCUMENTS

| | | | |
|---|---|---|---|
| 0000091 | 1/1987 | Japan | 544/235 |

*Primary Examiner*—Donald G. Daus
*Attorney, Agent, or Firm*—Oblon, Spivak, McClelland, Maier & Neustadt

[57] ABSTRACT

A thiadiazabicyclononane derivative having the formula:

(I)

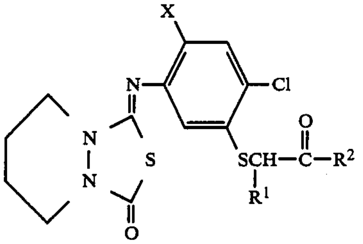

wherein X is hydrogen or halogen, $R^1$ is hydrogen or alkyl, $R^2$ is alkenyloxy, alkynyloxy, alkylthio, halogen-substituted alkoxy, alkoxycarbonylalkoxy, α,α-dimethylbenzylamino, $—OC_2H_4S(O)_lR^3$ (wherein $R^3$ is alkyl or phenyl, and l is an integer of 0 or 2),

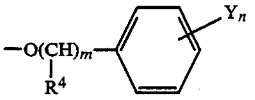

(wherein Y is halogen, alkyl, alkoxy or nitro, $R^4$ is hydrogen or alkyl, and each of m and n is an integer of 0, 1 or 2), $—OC_2H_4OR^5$ (wherein $R^5$ is phenyl, benzyl or methoxyalkyl), $—OCH_2R^6$ (wherein $R^6$ is styryl, cyanoalkyl, tetrahydrofuran-2-yl, thienyl or pyridin-2-yl),

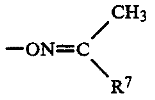

(wherein $R^7$ is alkyl or phenyl) or

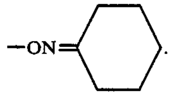

.

12 Claims, 4 Drawing Sheets

THIADIAZABICYCLONONANE DERIVATIVES AND HERBICIDAL COMPOSITIONS

The present invention relates to 9-phenylimino-8-thia-1,6-diazabicyclo-[4.3.0]nonan-7-one derivatives and herbicidal compositions containing them.

In recent years, a number of herbicides have been developed and actually used, and they have contributed to the reduction of the agricultural work load and to the improvement of the productivity. As a herbicide having a hetero ring, oxadiazon [i.e. 5-t-butyl-3-(2,4-dichloro-5-isopropoxyphenyl)-1,3,4-oxadiazolin-2-one] is widely used. However, oxadiazon is likely to bring about phytotoxicity, when used in paddy fields, and it is not effective against perennial weeds, particularly against *Sagittaria pygmaea.* When used in upland fields, it is not so safe against crop plants such as corn or soybean and has drawbacks that its herbicidal activities are low against hardly controllable weeds such as cocklebur or morning-glory and against pigweed and lambsquarters. Accordingly, a development of a herbicide having improved herbicidal activities and safety has been desired.

Under the circumstances, the present inventors have conducted extensive researches with an aim to develop a herbicide which satisfies the following conditions, and have finally accomplished the present invention.

(1) It is effective at a low dose.

(2) It is effective against paddy filed weeds and (or) against upland field weeds.

(3) It is also effective against perennial weeds and (or) hardly controllable weeds.

(4) It is effective in a wide range covering the germination stage to the growing stage.

(5) It has excellent residual effects and can be expected to provide stabilized effects.

(6) It is highly safe to crop plants.

Thus, the present invention provides a thiadiazabicyclononane derivative having the formula:

(I)

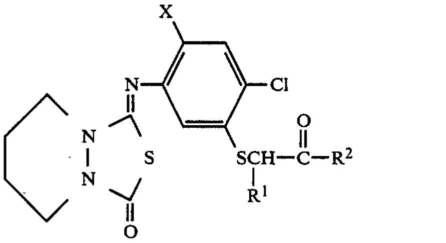

wherein X is hydrogen or halogen such as chlorine, bromine, fluorine or iodine, $R^1$ is hydrogen or alkyl, preferably $C_1$–$C_6$ alkyl, more preferably $C_1$–$C_4$ alkyl, $R^2$ is alkenyloxy, preferably $C_2$–$C_6$ alkenyloxy, alkynyloxy, preferably $C_2$–$C_6$ alkynyloxy, alkylthio, preferably $C_1$–$C_6$ alkylthio, more preferably $C_1$–$C_4$ alkylthio, halogen-substituted alkoxy, preferably halogen-substituted $C_1$–$C_6$ alkoxy, alkoxycarbonylalkoxy, preferably $C_1$–$C_4$ alkoxycarbonyl $C_1$–$C_4$ alkoxy, α,α-dimethylbenzylamino, $—OC_2H_4S(O)_lR^3$ (wherein $R^3$ is alkyl, preferably $C_1$–$C_4$ alkyl or phenyl, and l is an integer of 0 or 2),

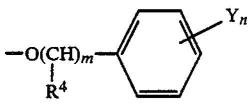

(wherein Y is halogen, alkyl, preferably $C_1$–$C_4$ alkyl, alkoxy, preferably $C_1$–$C_4$ alkoxy or nitro, $R^4$ is hydrogen or alkyl, preferably $C_1$–$C_4$ alkyl and each of m and n is an integer of 0, 1 or 2), $—OC_2H_4OR_5$ (wherein $R^5$ is phenyl, benzyl or methoxyalkyl, preferably methoxy $C_1$–$C_4$ alkyl), $—OCH_2R^6$ (wherein $R^6$ is styryl, cyanoalkyl, tetrahydrofuran-2-yl, thienyl or pyridin-2-yl),

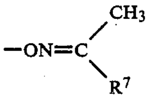

(wherein $R^7$ is alkyl, preferably $C_1$–$C_4$ alkyl, or phenyl)

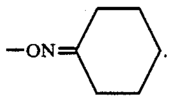

Figure 1:
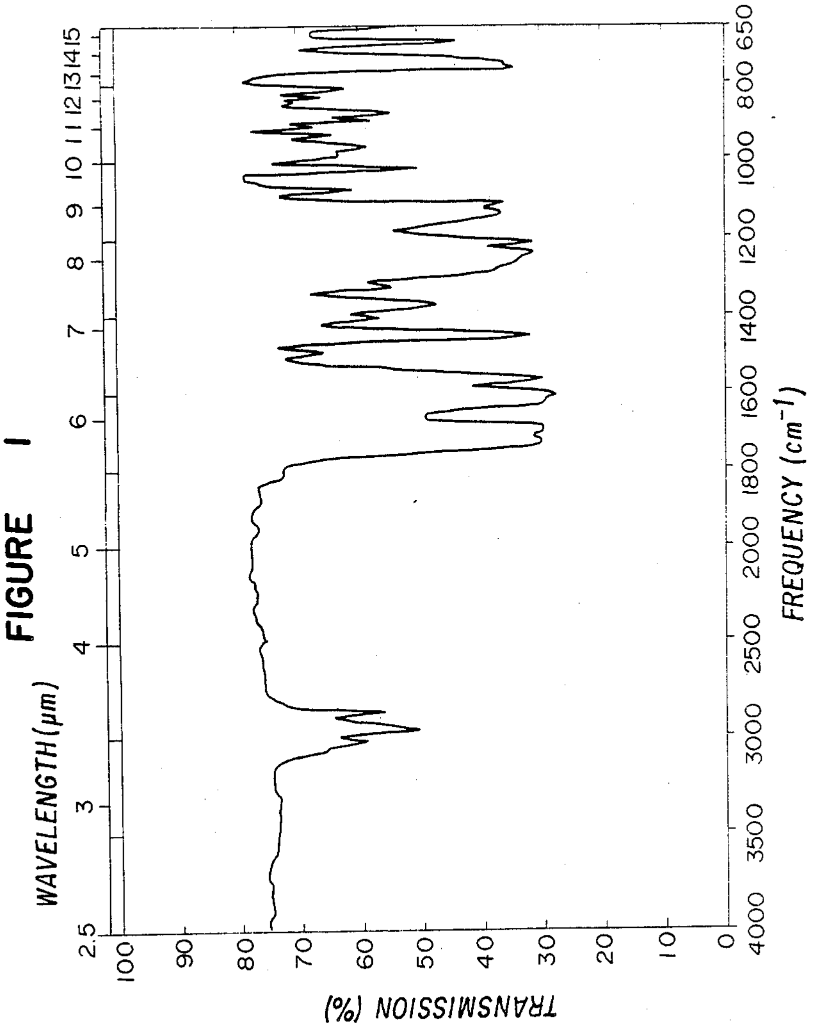
FIG. 1 is the infrared absorption spectrum of Compound 7.
Figure 2:
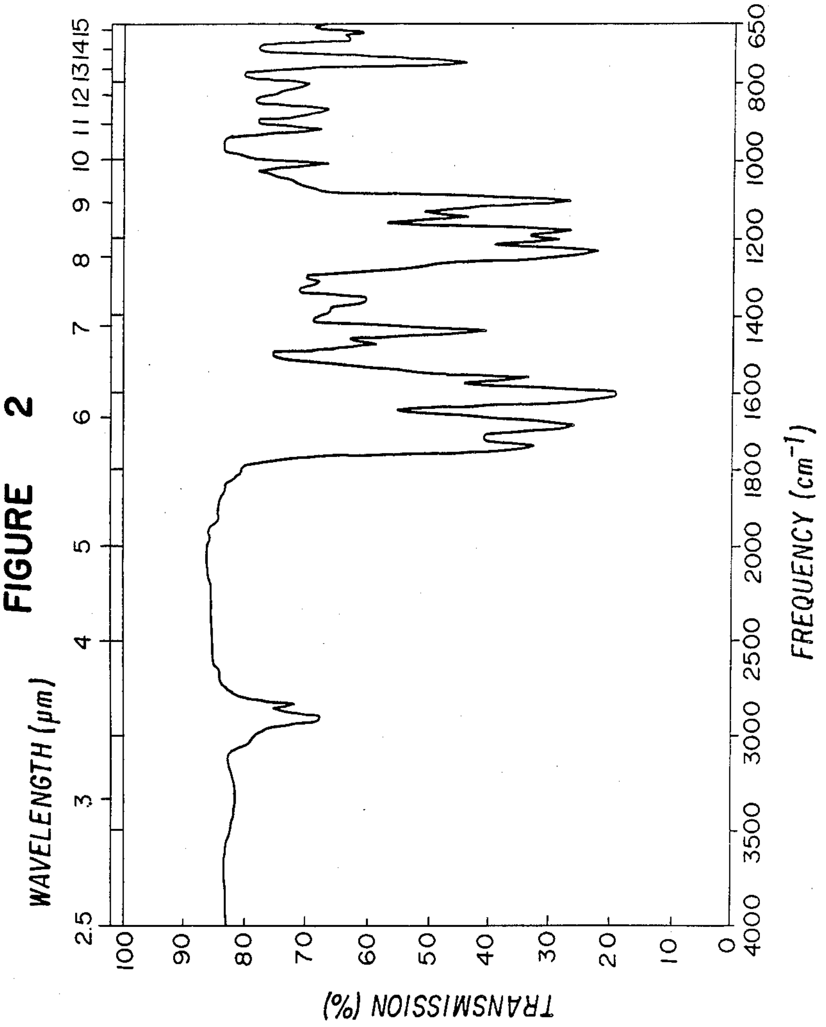
FIG. 2 is the infrared absorption spectrum of Compound 10.
Figure 3:
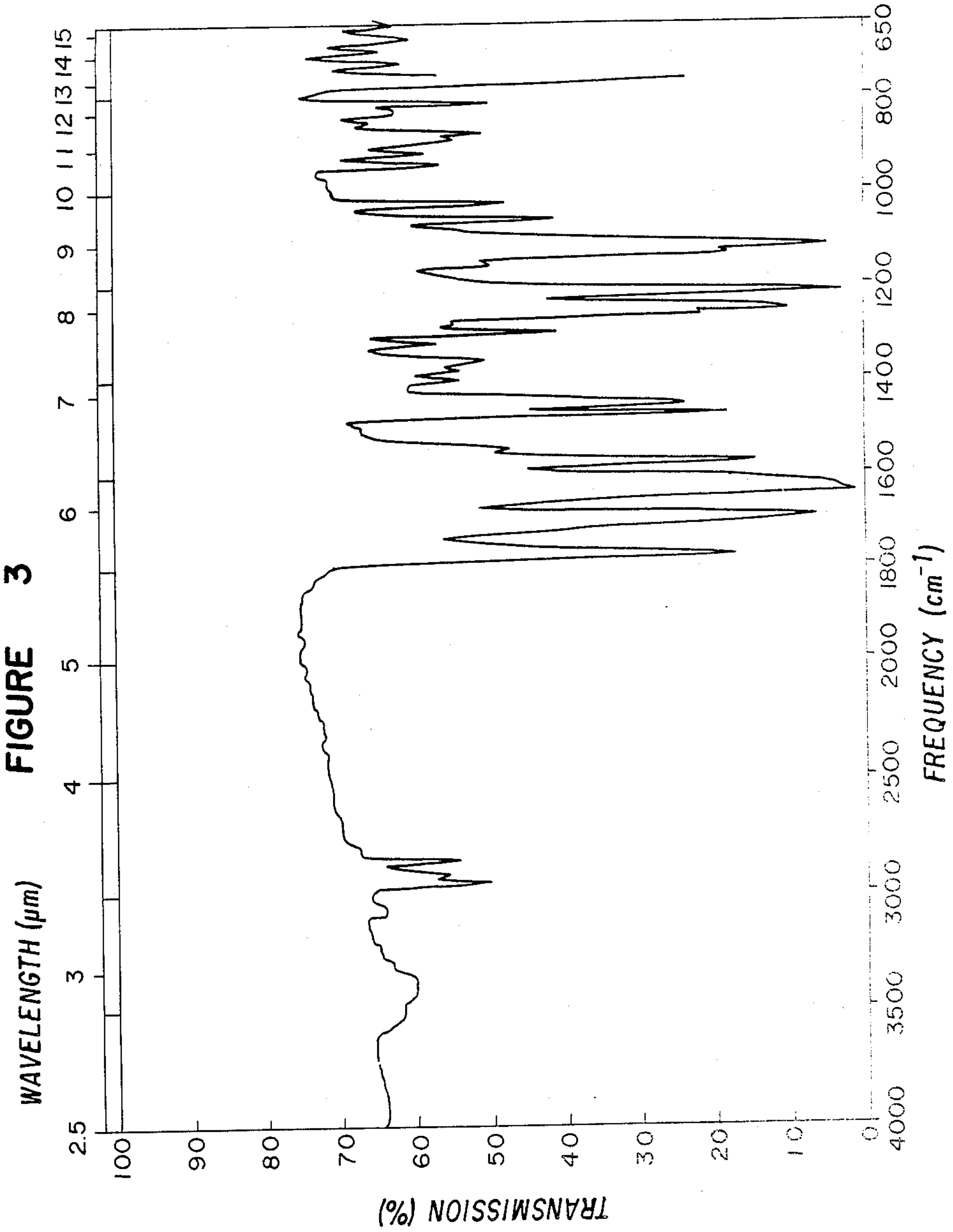
FIG. 3 is the infrared absorption spectrum of Compound 63.
Figure 4:
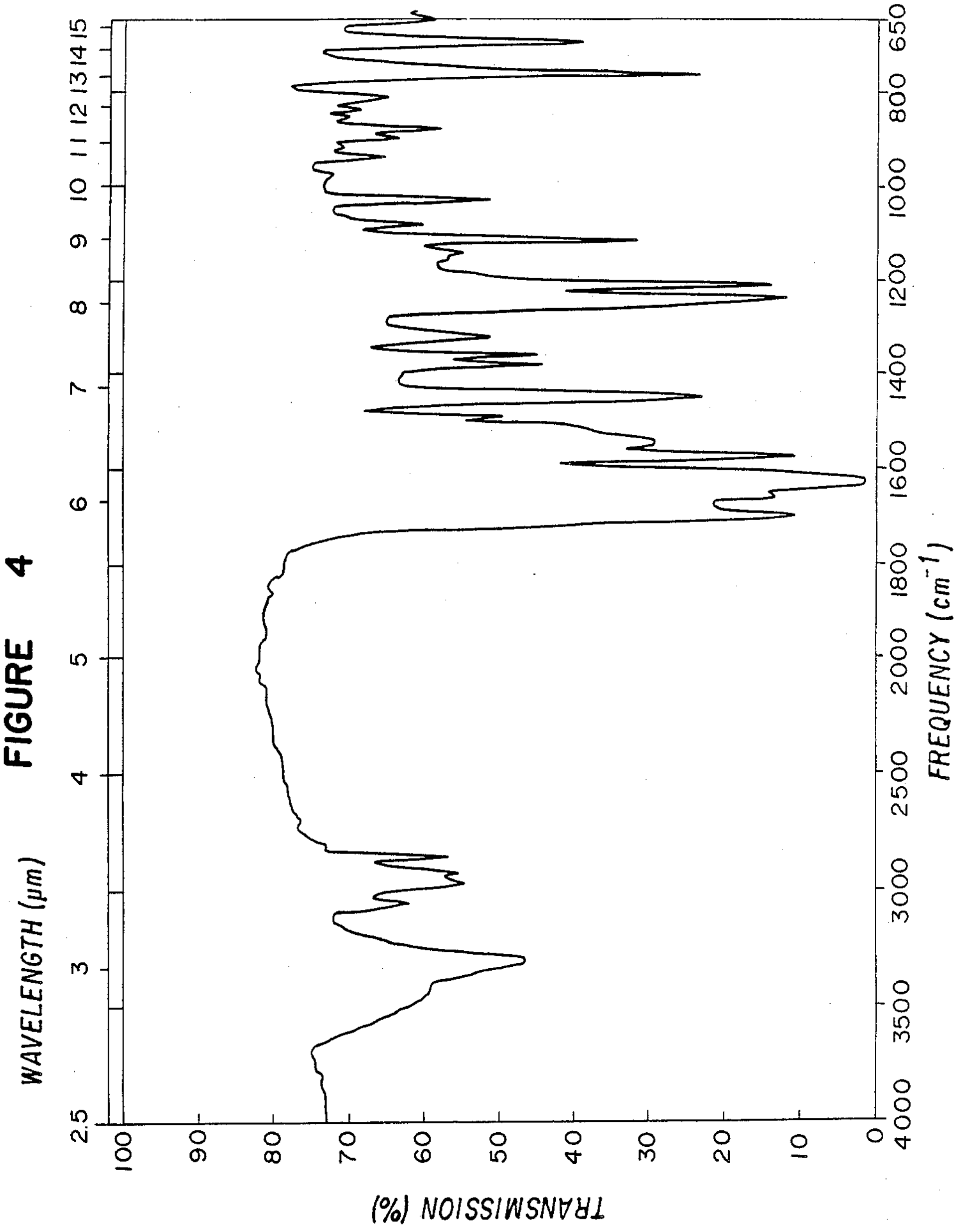
FIG. 4 is the infrared absorption spectrum of Compound 111.

Among the compounds of the present invention, preferred are compound of the formula I wherein X is hydrogen or halogen, particularly fluorine, $R^1$ is hydrogen, and $R^2$ is

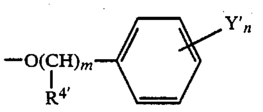

(wherein Y' is halogen, $R^{4'}$ is hydrogen or methyl and each of m and n is an integer of 0, 1 or 2), $—OC_2H_4OR^5$ (wherein $R^5$ is as defined above) or $—CH_2R^6$ (wherein $R^6$ is as defined above), particularly

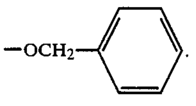

Now, typical examples of the compound of the formula I will be presented in Table 1. The compound Nos. indicated in the Table will be referred to in the subsequent description.

TABLE 1

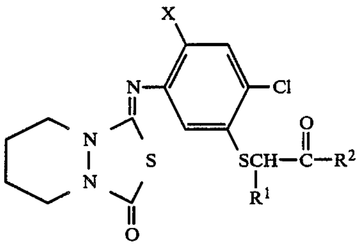

| Compound No. | X | $R^1$ | $R^2$ | Physical property refractive index($n_D^{20}$) or m.p.(°C.) |
|---|---|---|---|---|
| 1 | H | H | $OCH_2C{\equiv}CH$ | 105–107 |
| 2 | F | H | $OCH_2C{\equiv}CH$ | 1.5960 |
| 3 | H | $C_3H_7$ | $OCH_2C{\equiv}CH$ | 1.6064 |
| 4 | H | H | $OCH_2CH{=}CH_2$ | 86–88 |
| 5 | F | H | $OCH_2CH{=}CH_2$ | 1.6118 |
| 6 | H | $C_3H_7$ | $OCH_2CH{=}CH_2$ | 1.6011 |
| 7 | H | H | 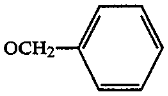 | 1.6158 |
| 8 | F | H | 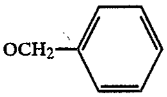 | 1.6279 |
| 9 | H | $C_3H_7$ | 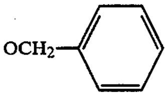 | 1.6181 |
| 10 | H | H | 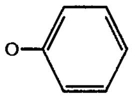 | Not measurable |
| 11 | F | H | 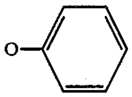 | 1.6293 |
| 12 | H | $C_3H_7$ | 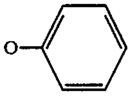 | 1.6122 |
| 13 | H | H | $SC_2H_5$ | 1.6160 |
| 14 | F | H | $SC_2H_5$ | 1.6280 |
| 15 | H | $C_3H_7$ | $SC_2H_5$ | 1.6080 |
| 16 | H | H | $OCH_2CH_2SCH_3$ | 57–58 |
| 17 | F | H | $OCH_2CH_2SCH_3$ | 78–80 |
| 18 | H | H | $OCH_2CH_2Cl$ | 1.6200 |
| 19 | F | H | $OCH_2CH_2Cl$ | 1.6147 |
| 20 | H | H | $OCH_2CH_2CH_2Cl$ | 1.6169 |
| 21 | F | H | $OCH_2CH_2CH_2Cl$ | 1.5995 |
| 22 | H | H | $OCH_2CH_2SC_2H_5$ | 52–54 |
| 23 | F | H | $OCH_2CH_2SC_2H_5$ | 75–78 |
| 24 | H | H | $OCH_2CH_2SC_3H_7$—i | 1.6061 |
| 25 | F | H | $OCH_2CH_2SC_3H_7$—i | 1.6021 |
| 26 | H | H | $OCHCO_2CH_3$<br>\|<br>$CH_3$ | 1.6017 |
| 27 | F | H | $OCHCO_2CH_3$<br>\|<br>$CH_3$ | 1.5892 |

TABLE 1-continued

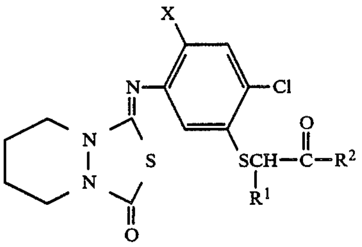

| Compound No. | X | $R^1$ | $R^2$ | Physical property refractive index($n_D^{20}$) or m.p.(°C.) |
|---|---|---|---|---|
| 28 | H | H | 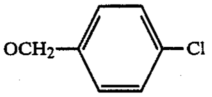 | 1.6430 |
| 29 | F | H | 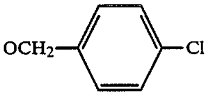 | 1.6264 |
| 30 | H | H | 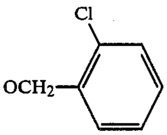 | 1.6238 |
| 31 | F | H | 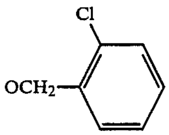 | 1.6130 |
| 32 | H | H | 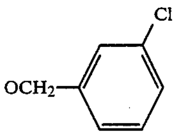 | 1.6400 |
| 33 | F | H | 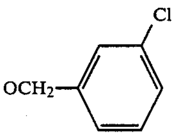 | 1.6310 |
| 34 | H | H | 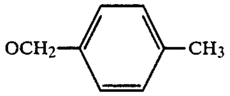 | 1.6339 |
| 35 | F | H | 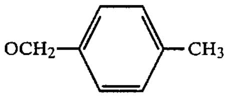 | 1.6196 |
| 36 | H | H | 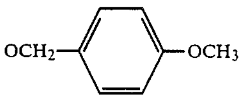 | 1.6298 |

TABLE 1-continued

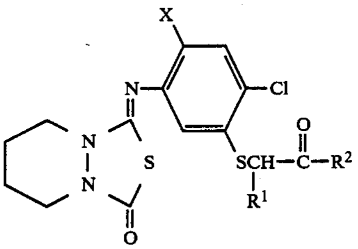

| Compound No. | X | $R^1$ | $R^2$ | Physical property refractive index($n_D^{20}$) or m.p.(°C.) |
|---|---|---|---|---|
| 37 | F | H | 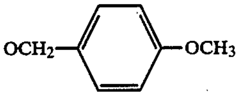 | 1.6200 |
| 38 | H | H | 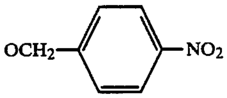 | 1.6399 |
| 39 | F | H | 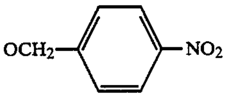 | 1.6298 |
| 40 | H | H | 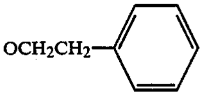 | 1.6374 |
| 41 | F | H | 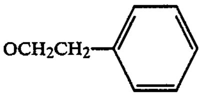 | 1.6191 |
| 42 | H | H | $OCH_2CH_2SO_2CH_3$ | 143-144 |
| 43 | F | H | $OCH_2CH_2SO_2CH_3$ | 155-156 |
| 44 | H | H | $OCH_2CF_3$ | 1.5910 |
| 45 | H | H | 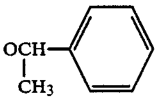 | 1.6127 |
| 46 | F | H | 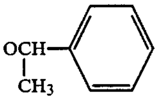 | 1.6200 |
| 47 | H | H | 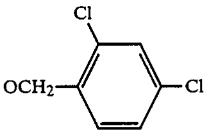 | 103-105 |
| 48 | F | H | 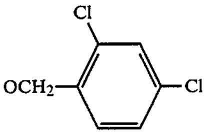 | 1.6075 |

TABLE 1-continued

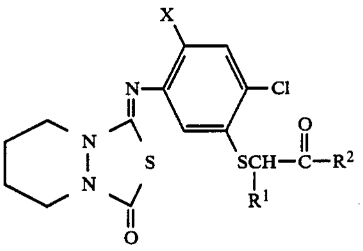

| Compound No. | X | $R^1$ | $R^2$ | Physical property refractive index($n_D^{20}$) or m.p.(°C.) |
|---|---|---|---|---|
| 49 | H | $CH_3$ | 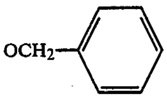 | 1.6225 |
| 50 | F | $CH_3$ | 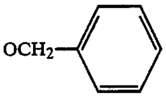 | 1.6100 |
| 51 | H | H | $OCH_2CH{=}CHCH_3$ | 1.6400 |
| 52 | F | H | $OCH_2CH{=}CHCH_3$ | 1.6050 |
| 53 | H | H | $OCH_2CO_2CH_3$ | 1.6160 |
| 54 | F | H | $OCH_2CO_2CH_3$ | 1.6009 |
| 55 | H | H | 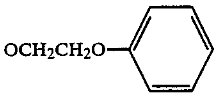 | 1.6302 |
| 56 | F | H | 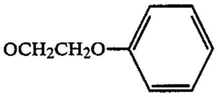 | 1.6220 |
| 57 | H | H | 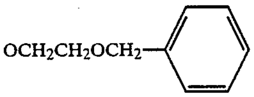 | 1.6235 |
| 58 | F | H | 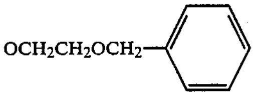 | 1.6060 |
| 59 | H | H | $OCH_2CH_2OC_2H_4OCH_3$ | 1.6062 |
| 60 | F | H | $OCH_2CH_2OC_2H_4OCH_3$ | 1.5951 |
| 61 | H | H | 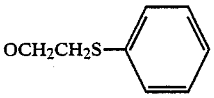 | 1.6469 |
| 62 | F | H | 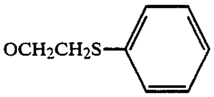 | 1.6385 |
| 63 | H | H | 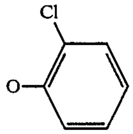 | Not measurable |

TABLE 1-continued
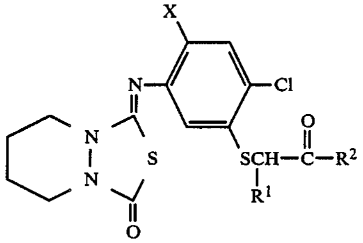
| Compound No. | X | $R^1$ | $R^2$ | Physical property refractive index($n_D^{20}$) or m.p.(°C.) |
|---|---|---|---|---|
| 64 | F | H | 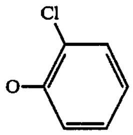 | 1.6311 |
| 65 | H | H | 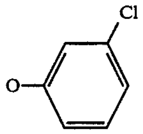 | 1.6261 |
| 66 | F | H | 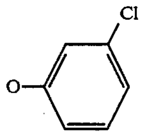 | 1.6298 |
| 67 | H | H | 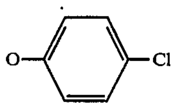 | 99–100 |
| 68 | F | H | 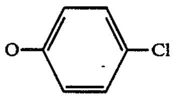 | 86–88 |
| 69 | H | H | 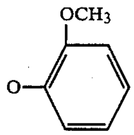 | 104–105 |
| 70 | F | H | 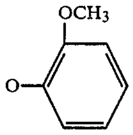 | 106–108 |
| 71 | H | H | 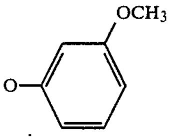 | 101–103 |
| 72 | F | H | 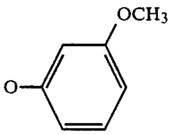 | 1.6269 |
TABLE 1-continued
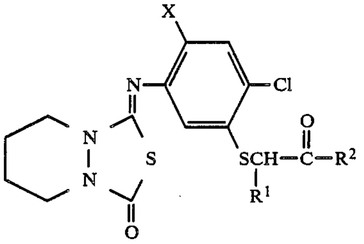
| Compound No. | X | $R^1$ | $R^2$ | Physical property refractive index($n_D^{20}$) or m.p.(°C.) |
|---|---|---|---|---|
| 73 | H | H | 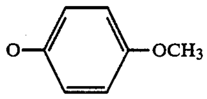 | 83–85 |
| 74 | F | H | 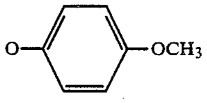 | 1.6309 |
| 75 | H | H | 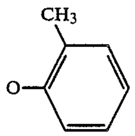 | 109–111 |
| 76 | F | H | 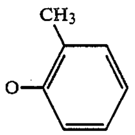 | 124–126 |
| 77 | H | H | 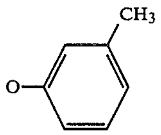 | 120–121 |
| 78 | F | H | 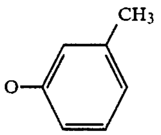 | 1.6161 |
| 79 | H | H | 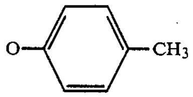 | 1.6388 |
| 80 | F | H | 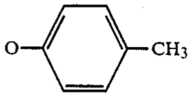 | 1.6280 |
| 81 | H | H | 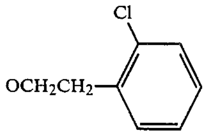 | 1.6329 |

TABLE 1-continued

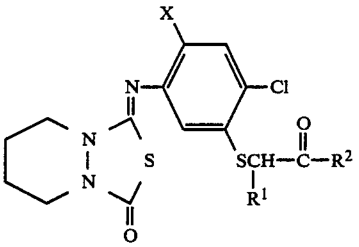

| Compound No. | X | R[1] | $R^2$ | Physical property refractive index($n_D^{20}$) or m.p.(°C.) |
|---|---|---|---|---|
| 82 | F | H | 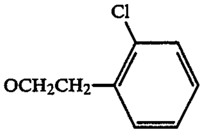 | 76–78 |
| 83 | H | H | 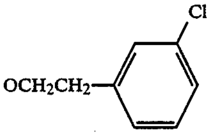 | 1.6175 |
| 84 | F | H | 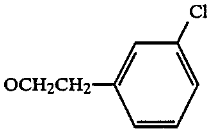 | 1.6165 |
| 85 | H | H | 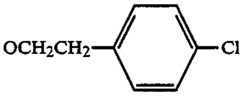 | 68–70 |
| 86 | F | H | 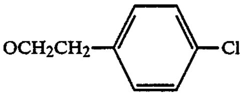 | 101–103 |
| 87 | H | H | 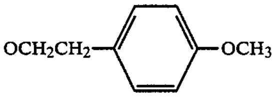 | 1.6145 |
| 88 | F | H | 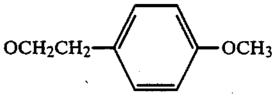 | 72–75 |
| 89 | H | H | $OCH_2CO_2C_2H_5$ | 1.6110 |
| 90 | F | H | $OCH_2CO_2C_2H_5$ | 1.6007 |
| 91 | H | H | $OCH(CH_3)CO_2C_2H_5$ | 1.5996 |
| 92 | F | H | $OCH(CH_3)CO_2C_2H_5$ | 1.5880 |
| 93 | H | H | $OCH(CH_3)CO_2C_4H_9$ | 1.5859 |
| 94 | F | H | $OCH(CH_3)CO_2C_4H_9$ | 1.5729 |
| 95 | H | H | 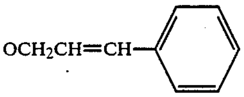 | 1.6438 |
| 96 | F | H | 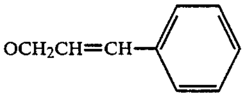 | 1.6210 |

TABLE 1-continued

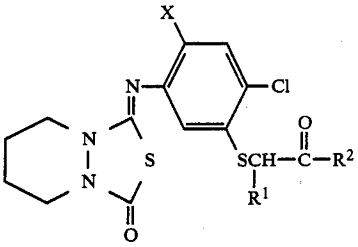

| Compound No. | X | R[1] | $R^2$ | Physical property refractive index($n_D^{20}$) or m.p.(°C.) |
|---|---|---|---|---|
| 97 | H | H | $OCH_2CH_2CN$ | 1.6270 |
| 98 | F | H | $OCH_2CH_2CN$ | 1.6088 |
| 99 | H | H | 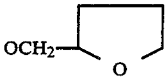 | 1.6000 |
| 100 | F | H | 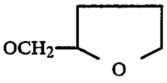 | 1.5862 |
| 101 | H | H | 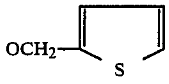 | 1.6490 |
| 102 | F | H | 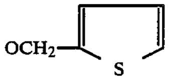 | 82–84 |
| 103 | H | H | 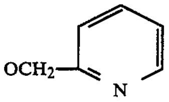 | 1.6439 |
| 104 | F | H | 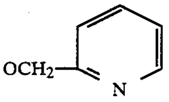 | 1.6070 |
| 105 | H | H | $ON{=}C(CH_3)_2$ | 1.6264 |
| 106 | F | H | $ON{=}C(CH_3)_2$ | 1.5975 |
| 107 | H | H | $ON{=}C(CH_3)C_2H_5$ | 1.6100 |
| 108 | F | H | $ON{=}C(CH_3)C_2H_5$ | 1.6240 |
| 109 | H | H | 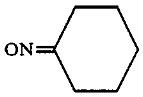 | 1.6158 |
| 110 | F | H | 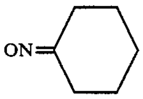 | 1.6050 |
| 111 | H | H | 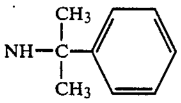 | Not measurable |
| 112 | F | H | 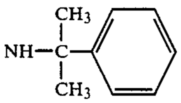 | 76–78 |

TABLE 1-continued

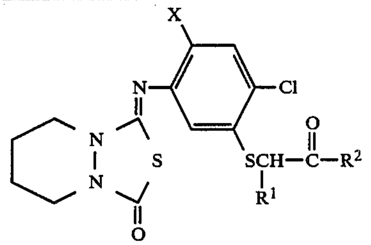

| Compound No. | X | $R^1$ | $R^2$ | Physical property refractive index($n_D^{20}$) or m.p.(°C.) |
|---|---|---|---|---|
| 113 | H | H | $ON{=}C(CH_3)$— 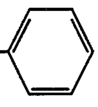 | 1.6250 |
| 114 | F | H | $ON{=}C(CH_3)$— 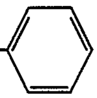 | 1.6315 |

The compound of the formula I of the present invention can be prepared by the following process.

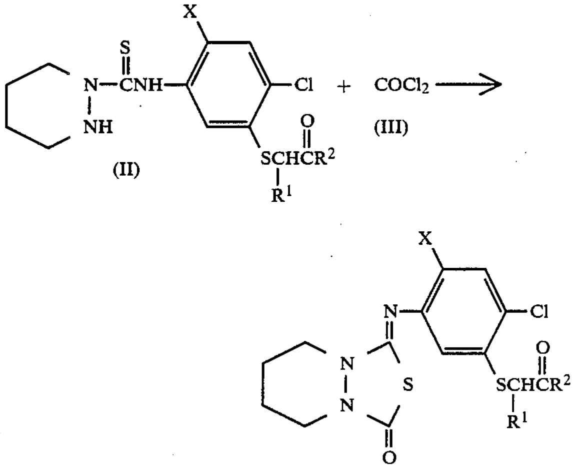

(II) (III) (I)

In the above formulas, X, $R^1$ and $R^2$ are as defined above. The process can be conducted by reacting the compound of the formula II with the compound of the formula III in the presence of a base.

As the base, there may be mentioned an aliphatic tertiary amine such as triethylamine or trimethylamine; an aromatic tertiary amine such as pyridine, picoline or quinoline; or an inorganic base such as sodium hydroxide, potassium hydroxide, potassium carbonate or sodium carbonate.

The above reaction is preferably conducted in a solvent. As such a solvent, there may be mentioned a chlorine-containing hydrocarbon such as dichloromethane, chloroform or carbon tetrachloride; and an ether such as diethyl ether, tetrahydrofuran or dioxane; a hydrocarbon such as n-hexane, benzene or toluene; an aliphatic ketone such as acetone or methyl ethyl ketone; dimethylsulfoxide; or N,N-dimethylformamide.

The above reaction can be completed in from 1 to 7 hours at a temperature within a range of from −20° C. to the boiling point of the solvent.

The compound of the formula II can be prepared, for example, by the following process.

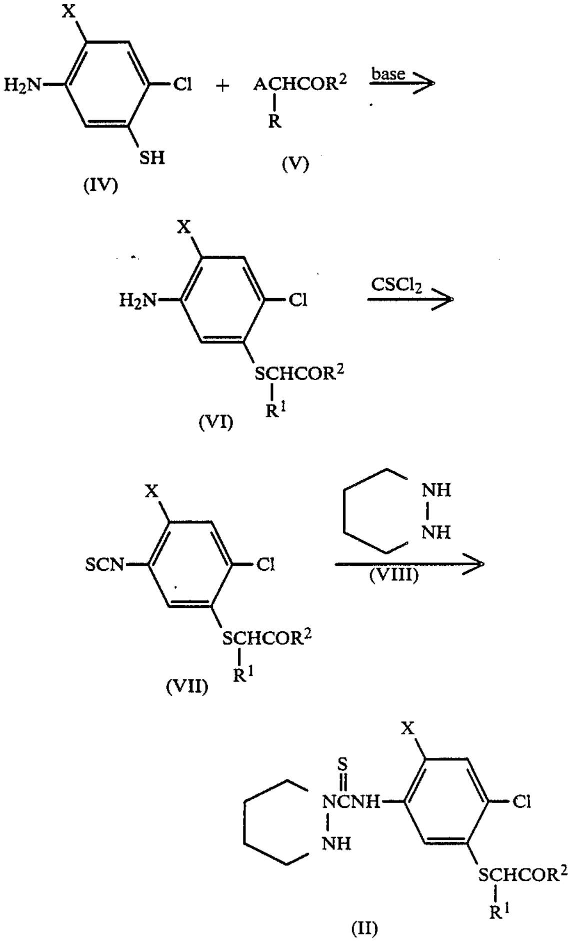

(IV) (V) (VI) (VII) (VIII) (II)

In the above formulas, X, $R^1$ and $R^2$ are as defined above. The intermediate of the formula VI can be obtained in good yield by reacting the compound of the formula IV with the compound of the formula V in the presence of a base. As a solvent used for this reaction, there may be employed, for example, a lower aliphatic acid amide such as acetonitrile, dimethylformamide or dimethylacetamide, dimethylsulfoxide, water, an ether such as tetrahydrofuran or dioxane, an aliphatic acid ester such as ethyl acetate, an alcohol such as methanol, ethanol, propanol or glycol or a ketone such as acetone, methyl ethyl ketone or cyclohexanone. As the base, there may be mentioned an inorganic base such as potassium carbonate, sodium hydrogencarbonate, an alkali metal alcoholate or an alkali metal, or an organic base such as pyridine, trimethylamine, triethylamine, diethylaniline or 1,8-diazabicyclo[5,4,0]-7-undecene. The reaction can be conducted at a temperature within a range of from 0° C. to the boiling point of the solvent for a reaction time within a range of from 30 minutes to 24 hours, preferably from 1 to 4 hours.

Further, the intermediate of the formula VII can be obtained in good yield by reacting the compound of the formula VI with thiophosgene in a two phase system comprising an aqueous phase and an organic phase. As the organic solvent used for this reaction, there may be employed, for example, a halide such as dichloromethane chloroform or carbon tetrachloride, an aromatic hydrocarbon such as toluene or benzene or an aliphatic acid ester such as ethyl acetate. The reaction can be conducted at a temperature within a range of from 0° C. to the boiling point of the solvent for a reaction time within a range of from 30 minutes to 24 hours, preferably from 1 to 4 hours.

Further, the intermediate of the formula II can be obtained in good yield by reacting the compound of the formula VII with the compound of the formula VIII in a solvent. As the solvent for the reaction, there may be mentioned a halide such as dichloromethane, chloroform or carbon tetrachloride, water, an ether such as tetrahydrofuran or dioxane or an aliphatic acid ester such as ethyl acetate. The reaction can be conducted at a temperature within a range of from 0° to the boiling point of the solvent for a reaction time within a range of from 30 minutes to 24 hours, preferably from 1 to 4 hours.

The compound of the formula VIII was prepared in accordance with the method disclosed in Bull. Soc. Chin. Fvance, P. 704 (1957).

The compound of formula I of the present invention can be prepared by the following process as another process.

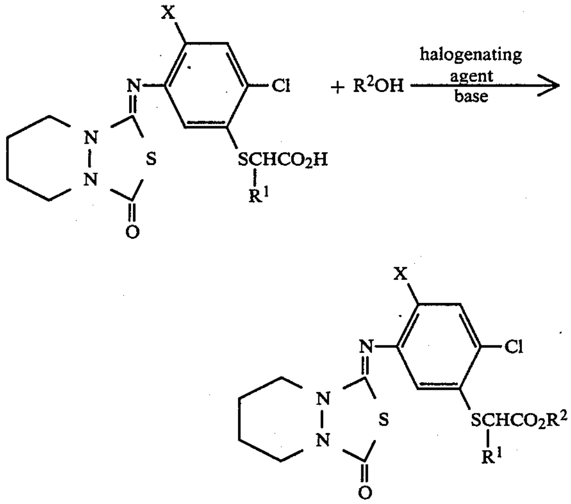

In the above formulas, X, $R^1$ and $R^2$ are as defined above. The compound of the formula I of the present invention can be obtained by the reaction of the compound of the formula IX with the compound of the formula X in the presence of a Billsmayer reagent and a base. As the solvent used for the reaction, there may be used a lower aliphatic acid amide such as dimethylformamide or diethylformamide or a halide such as dichloromethane, chloroform or carbon tetrachloride. As the halogenating agent, there may be mentioned phosphorus oxychloride, thionyl chloride, oxalyl chloride or phosgene. As the base, there may be mentioned an organic base such as pyridine, trimethylamine, triethylamine, diethylaniline or 1,8-diazabicyclo[5,4,0]-7-undecene or an inorganic base such as potassium carbonate, sodium carbonate, sodium hydrogencarbonate or an alkali metal alcoholate. The reaction can be conducted at a temperature within a range of from −30° to 30° C. for a reaction time within a range of from 30 minutes to 24 hours, preferably from 4 to 14 hours.

Now, the present invention will be described in further detail with reference to Preparation Examples. However, it should be understood that the present invention is by no means restricted by these specific Preparation Examples.

PREPARATION EXAMPLE 1

Preparation of 9-(4-chloro-3-propargyloxycarbonylmethylthiophenylimino)-8-thia-1,6-diazabicyclo[4.3.0]nonan-7-one Into a reaction flask, 0.7 g (1.8 mmol) of 1,2-tetramethylene-1-(4-chloro-3-propargyloxycarbonylmethylthiophenylaminothiocarbonyl)hydrazine, 0.5 g (6 mmol) of pyridine and 20 ml of dichloromethane were charged, and a dichloromethane solution containing 0.3 g (3 mmol) of phosgene was dropwise added thereto. After the dropwise addition, the mixture was stirred at room temperature for one hour to complete the reaction. After the completion of the reaction, the reaction solution was washed with water and dried over anhydrous magnesium sulfate. Then, the solvent was distilled off to obtain a crude product. This crude product was purified by silica gel column chromatography to obtain 0.3 g (yield: 41%) of the desired compound as white crystals. Melting point: 105° to 107° C.

PREPARATION EXAMPLE 2

Preparation of 9-(4-chloro-3-benzyloxycarbonylmethylthiophenylimino)-8-thia-1,6-diazabicyclo[4.3.0]nonan-7-one Into a reaction flask, 1.4 g (3.2 mmol) of 1,2-tetramethylene-1-(4-chloro-3-benzyloxycarbonylmethylthiophenylaminothiocarbonyl)hydrazine, 0.8 g (10 mmol) of pyridine and 20 ml of dichloromethane were charged, and a dichloromethane solution containing 0.5 g (5 mmol) of phosgene was dropwise added while cooling the mixture with ice water. After the dropwise addition, the mixture was stirred at room temperature for one hour to complete the reaction. After the completion of the reaction, the reaction solution was washed with water and dried over anhydrous magnesium sulfate. Then, the solvent was distilled off to obtain a crude product. This crude product was purified by silica gel column chromatography to obtain 1.0 g (yield: 67%) of the desired compound as colorless viscous substance. Refractive index $n_D^{20}$: 1.6158.

PREPARATION EXAMPLE 3

Preparation of 9-[4-chloro-3-(2-methylthioethoxycarbonylmethylthio)phenylimino]-8-thia-1,6-diazabicyclo[4.3.0]-nonan-7-one Into a reaction flask, 1.4 g (3.3 mmol) of 1,2-tetramethylene-1-[4-chloro-3-(2-methylthioethoxycarbonylmethylthio)phenylaminothiocarbonyl]hydrazine, 0.8 g (10 mmol) of pyridine and 20 ml of dichloromethane were charged, and a dichloromethane solution containing 0.5 g (5 mmol) of phosgene was dropwise added while cooling the mixture with ice water. After the dropwise addition, the mixture was stirred at room temperature for one hour to complete the reaction. After the completion of the reaction, the reaction solution was washed with water and dried over anhydrous magnesium sulfate. Then, the solvent was distilled off to obtain a crude product. This crude product was purified by silica gel column chromatography to obtain 0.7 g (yield: 47%) of the desired compound as white crystals. Melting point: 57° to 58° C.

PREPARATION EXAMPLE 4

Preparation of 9-(4-chloro-2-fluoro-5-isopropyridene-aminooxycarbonylmethylthiophenylimino)-8-thia-1,6-diazabicyclo[4.3.0]nonan-7-one Into a reaction flask, 2.5 g (6.4 mmol) of 1,2-tetramethylene-1-(4-chloro-2-fluoro-5-isopropyrideneaminooxycarbonylmethylthiophenylaminothiocarbonyl)hydrazine and 10 ml of DMF were charged, and 0.8 g (6.7 mmol) of thionyl chloride was dropwise added while cooling the mixture with ice water. After the dropwise addition, the mixture was stirred at 0° C. for 30 minutes, the 50 ml of $CH_2Cl_2$ was added thereto, and 10 ml of a $CH_2Cl_2$ solution of 0.5 g (6.8 mmol) of acetone oxime was dropwise added thereto at 0° C. After the dropwise addition, the mixture was stirred at 0° C. for 30 minutes, and then 1 g (12.8 mmol) of pyridine was dropwise added thereto at 0° C. Then, the mixture was stirred at room temperature for 12 hours. After the completion of the reaction, the reaction solution was dissolved in ethyl acetate, and the solution was washed with water and dried over anhydrous magnesium sulfate. Then, the solvent was distilled off to obtain a crude product. This crude product was purified by silica gel column chromatography to obtain 1.2 g (yield: 42.1%) of slightly brown viscous liquid. Refractive index $n_D^{20}$: 1 5975.

PREPARATION EXAMPLE 5

Preparation of 9-(4-chloro-2-fluoro-5-thienyloxycarbonyl-methythiophenylimino)-8-thia-1,6-diazabicyclo[4.3.0]-nonan-7-one Into a reaction flask, 1 g (2.2 mmol) of 1,2-tetramethylene-1-(4-chloro-2-fluoro-5-thienyloxycarbonylmethylthiophenylaminothiocarbonyl)hydrazine, 0.5 g (6 mmol) of pyridine and 20 ml of dichloromethane were charged and a dichloromethane solution containing 0.5 g (5 mmol) of phosgene was dropwise added while cooling the mixture with ice water. After the dropwise addition, the mixture was stirred at room temperature for one hour to complete the reaction. After the completion of the reaction, the reaction solution was washed with water and dried over anhydrous magnesium sulfate. Then, the solvent was distilled off to obtain a crude product. This crude product was purified by silica gel column chromatography to obtain 0.8 g (yield: 74.8%) of white crystals. Melting point: 82° to 84° C.

The herbicidal composition of the present invention comprises the 9-phenylimino-8-thia-1,6-diazabicyclo[4.3.0]nonan-7-one derivative of the formula I as an active ingredient and a carrier.

When the compound of the formula I of the present invention is used as a herbicide for a paddy rice field, the active ingredient can be used in a suitable formulation depending upon the particular purpose. Usually, the active ingredient is diluted with an inert liquid or solid carrier, and used in the form of a formulation such as a dust, a wettable powder, an emulsifiable concentrate, a granule, etc., if necessary, by adding a surfactant and other additives. Further, the compound of the present invention may be used in combination with an insecticide, a fungicide, other herbicides, a plant growth controlling agent, a fertilizer, etc., as the case requires.

Now, the formulations will be described in detail with reference to typical Formulation Examples. In the following Formulation Examples, "parts" means "parts by weight".

FORMULATION EXAMPLE 1 Wettable powder 10 parts of Compound No. 1, 0.5 part of Emulgen (trademark of Kao Corporation) 810, 0.5 part of Demol (trademark of Kao Corporation) N, 20 parts of Kunilite (trademark of Kunimine Industries Co., Ltd.) 201, and 69 parts of Zeeklite (trademark of Zeeklite Co., Ltd.) CA, were mixed and pulverized to obtain a wettable powder.

FORMULATION EXAMPLE 2 Wettable powder 10 parts of Compound No. 2, 0.5 part of Emulgen 810, 0.5 part of Demol N, 20 parts of Kunilite 201, 5 parts of Carplex 80 and 64 parts of Zeeklite CA, were mixed and pulverized to obtain a wettable powder.

FORMULATION EXAMPLE 3 Emulsifiable concentrate

To 30 parts of Compound No. 3, 60 parts of a mixture of xylene and isophorone in equal amounts and 10 parts of surfactant Sorpol (trademark of Toho Chemical Industry Co., Ltd.) 800A, were added, and the mixture was thoroughly mixed to obtain an emulsifiable concentrate.

FORMULATION EXAMPLE 4 Granules 10 parts of water was added to 10 parts of Compound No. 4, 80 parts of a filler obtained by mixing talc and bentonite in a ratio of 1:3 and 5 parts of fine silica, and the mixture was thoroughly kneaded to obtain a paste, which was extruded from sieve openings having a diameter of 0.7 mm and dried, and then cut into a length of from 0.5 to 1 mm to obtain granules.

The compounds of the present invention exhibit excellent herbicidal effects at a very low dose in a wide range from the germination stage to the growing stage of annual weeds such as barnyardgrass (*Echinochloa crus-galli*), umbrella-plant (*Cyperus difformis* L.), monochoria (*Monochoria vaginalis* Presl), spike-flowered rotala (*Rotala indica* Koehne), false pimpernel (*Lindernia procumbens* Philcox) and abunome (*Dopatrium junceum* Hamilt), and perennial weeds such as bulrush (*Scirpus juncoides* Roxb.), slender spikerush (*Eleocharis acicularis* Roem. et Schult.), water-plantain (*Alisma canaliculatm* A. Br. et Bouche), sagittaria (*Sagittaria pygmaea* Miq.) and cyperus sp. (*Cyperus serotinus* Rottb.) which grow in paddy fields. At the same time, they are highly safe to paddy field rice. Further, they exhibit high herbicidal effects, by soil treatment or by foliage treatment, against various weeds in the upland fields, for example, broad leaf weeds such as smartweed (*Polygonum nodosum* L.), pigweed (*Amaranthus retroflexus*). lambsquarters (*Chenopodium album*), speed-well (*Veronica persica*), wild mustard (*Brassica kaber* var. *pinnatifida*), cocklebur (*Xanthium strumarium*), morningglory (*Ipomoea spp*), hemp sesbania (*Sesbania exaltata* Raf.) and velvetleaf (*Abtilon theophrasti*), cyperaceous weeds such as rice flatsedge (*Cyperus iria L.*), and gramineous weeds such as barnyardgrass, large crabgrass (*Digitaria sanguinalis*) and green foxtail (*Setaria viridis*). At the same time, they have a feature that they are highly safe to crop plants such as soybean, corn, upland rice and wheat.

The compounds of the present invention have excellent residual effects, and show stabilized effects for a long period of time also in paddy fields. They are also useful for orchard, grassland, lawn and non-agricultural fields.

The dose of the compound of the present invention is usually within a range of from 1 g to 10 kg/ha. More specifically, the dose is usually from 5 g to 5 kg/ha for upland fields, from 10 g to 1 kg/ha for paddy rice fields, and from 200 g to 5 kg/ha for non-agricultural fields.

Now, the herbicidal effects of the herbicides of the present invention will be described with reference to Test Examples.

TEST EXAMPLES 1

Herbicidal test by soil treatment of paddy field

Into a porcelain pot having a diameter of 10 cm, paddy field soil was filled and puddled. Then seeds of barnyardgrass (Ec), umbrella plant (Cy), monochoria (Mo) and bulrush (Sc) were sown, and water was introduced to a depth of 3 cm.

Next day, the wettable powder prepared in accordance with Formulation Example 1, was diluted with water and dropwise applied to the surface of the water. The amount of the active ingredient applied, was 400 g/10 a. Then, the pot was left in a green house. Twenty one days after the application, the herbicidal effects were evaluated in accordance with the standards identified in Table 2.

As the result, Compound Nos. 1 to 114 of the present invention exhibited the herbicidal activities at a level of index 5.

TABLE 2

| Index | Herbicidal effects and phytotoxicity |
|---|---|
| 5 | Withered |
| 4.5 | Herbicidal effect (or phytotoxicity) in a range of 90 to 99% |
| 4 | Herbicidal effect (or phytotoxicity) in a range of 80 to 89% |
| 3.5 | Herbicidal effect (or phytotoxicity) in a range of 70 to 79% |
| 3 | Herbicidal effect (or phytotoxicity) in a range of 60 to 69% |
| 2.5 | Herbicidal effect (or phytotoxicity) in a range of 50 to 59% |
| 2 | Herbicidal effect (or phytotoxicity) in a range of 40 to 49% |
| 1.5 | Herbicidal effect (or phytotoxicity) in a range of 30 to 39% |
| 1 | Herbicidal effect (or phytotoxicity) in a range of 20 to 29% |
| 0.5 | Herbicidal effect (or phytotoxicity) in a range of 1 to 19% |
| 0 | No herbicidal effect (or no phytotoxicity) |

TEST EXAMPLE 2

Herbicidal test in soil treatment of upland field

Into a 120 $cm^2$ plastic pot, upland field soil was filled, and seeds of smart-weed (Po), slender amaranth (Am), lambsquarters (Ch) and rice flatsedge (Cy) were sown and covered with soil.

A wettable powder of each test compound formulated in accordance with Formulation Example 1, was diluted with water in an amount of 100 liter/10 a and uniformly applied to the surface of soil by means of a small size spray at a dose of 400 g/10 a of the active ingredient. After the application, the pot was left for 21 days in a green house, and then the herbicidal effects were evaluated in accordance with the standards identified in Table 2. The results are shown in Tables 3 and 4.

TABLE 3

| Compound | Herbicidal effects | | | |
|---|---|---|---|---|
| No. | Po | Am | Ch | Cy |
| 2 | 5 | 5 | 5 | 5 |
| 3 | 5 | 5 | 5 | 4 |
| 4 | 3 | 5 | 5 | 5 |
| 6 | 5 | 5 | 5 | 5 |
| 7 | 4 | 5 | 5 | 5 |
| 8 | 5 | 5 | 5 | 5 |
| 10 | 4 | 5 | 5 | 4 |
| 11 | 5 | 5 | 5 | 5 |
| 13 | 4 | 5 | 5 | 5 |
| 14 | 5 | 5 | 5 | 5 |
| 15 | 5 | 5 | 5 | 5 |
| 16 | 5 | 5 | 5 | 5 |
| 17 | 5 | 5 | 5 | 5 |
| 49 | 5 | 5 | 5 | 5 |
| 50 | 5 | 5 | 5 | 5 |

TABLE 4

| Compound | Herbicidal effects | | | |
|---|---|---|---|---|
| No. | Po | Am | Ch | Cy |
| 55 | 5 | 5 | 5 | 5 |
| 56 | 5 | 5 | 5 | 5 |
| 57 | 5 | 5 | 5 | 5 |
| 58 | 5 | 5 | 5 | 5 |
| 59 | 5 | 5 | 5 | 5 |
| 60 | 5 | 5 | 5 | 5 |
| 61 | 5 | 5 | 5 | 5 |
| 62 | 5 | 5 | 5 | 5 |
| 63 | 5 | 5 | 5 | 4 |
| 65 | 5 | 5 | 5 | 5 |
| 66 | 5 | 5 | 5 | 5 |
| 67 | 5 | 5 | 5 | 5 |
| 69 | 5 | 4 | 5 | 5 |
| 70 | 5 | 5 | 5 | 5 |
| 71 | 5 | 5 | 5 | 5 |
| 72 | 5 | 5 | 5 | 5 |
| 73 | 5 | 5 | 5 | 5 |
| 74 | 5 | 5 | 5 | 5 |
| 75 | 5 | 5 | 5 | 5 |
| 78 | 5 | 5 | 5 | 5 |
| 79 | 5 | 5 | 5 | 5 |
| 80 | 5 | 5 | 5 | 5 |
| 87 | 5 | 5 | 5 | 5 |
| 89 | 5 | 5 | 5 | 5 |
| 90 | 5 | 5 | 5 | 5 |
| 91 | 5 | 5 | 5 | 5 |
| 92 | 5 | 5 | 5 | 5 |
| 93 | 5 | 5 | 5 | 5 |
| 94 | 5 | 5 | 5 | 5 |
| 95 | 5 | 5 | 5 | 5 |
| 96 | 5 | 5 | 5 | 5 |
| 97 | 5 | 5 | 5 | 5 |
| 98 | 5 | 5 | 5 | 5 |
| 99 | 4 | 5 | 5 | 5 |
| 100 | 5 | 5 | 5 | 5 |
| 101 | 5 | 5 | 5 | 5 |
| 102 | 5 | 5 | 5 | 5 |
| 103 | 5 | 5 | 5 | 5 |
| 104 | 5 | 5 | 5 | 5 |
| 105 | 4 | 5 | 5 | 5 |
| 106 | 5 | 5 | 5 | 5 |
| 107 | 5 | 5 | 5 | 5 |
| 108 | 5 | 5 | 5 | 5 |
| 109 | 5 | 5 | 5 | 5 |
| 110 | 5 | 5 | 5 | 5 |
| 112 | 5 | 5 | 5 | 5 |
| 113 | 5 | 5 | 5 | 5 |
| 114 | 5 | 5 | 5 | 5 |

TEST EXAMPLE 3

Herbicidal test in foliage treatment in upland field

Into a 120 $cm^2$ plastic pot, upland field soil was filled, and seeds of barnyardgrass (Ec), smart-weed (Po), slender amaranth (Am), lambsquarters (Ch) and rice flatsedge (Cy) were sown, and grown in a green house until barnyardgrass grew to the 3 leaf stage. When barnyardgrass reached the 3 leaf stage, a wettable powder of each test compound formulated in accordance with Formulation Example 1 was diluted with water in an amount of 100 liter/10 a and applied to the foliage of the plants from above by a small size spray at a dose of 400 g/10 a of the active ingredient. After the application, the pot was left for 21 days in a green house, and then the herbicidal effects were evaluated in accordance with the standards identified in Table 2. The results are shown in Tables 5 and 6.

TABLE 5

| Compound | Herbicidal effects | | | | |
|---|---|---|---|---|---|
| No. | Ec | Po | Am | Ch | Cy |
| 1 | 4 | 5 | 5 | 5 | 5 |
| 2 | 5 | 5 | 5 | 5 | 5 |
| 3 | 5 | 5 | 5 | 5 | 5 |
| 4 | 4 | 5 | 5 | 5 | 5 |
| 5 | 5 | 5 | 5 | 5 | 5 |
| 6 | 5 | 5 | 5 | 5 | 5 |
| 7 | 5 | 5 | 5 | 5 | 5 |
| 8 | 5 | 5 | 5 | 5 | 5 |
| 9 | 5 | 5 | 5 | 5 | 5 |
| 10 | 5 | 5 | 5 | 5 | 5 |
| 11 | 5 | 5 | 5 | 5 | 5 |
| 12 | 5 | 5 | 5 | 5 | 4 |
| 13 | 5 | 5 | 5 | 5 | 5 |
| 14 | 5 | 5 | 5 | 5 | 5 |
| 15 | 5 | 5 | 5 | 5 | 5 |
| 16 | 5 | 5 | 5 | 5 | 5 |
| 17 | 5 | 5 | 5 | 5 | 5 |
| 49 | 5 | 5 | 5 | 5 | 5 |
| 50 | 5 | 5 | 5 | 5 | 5 |

TABLE 6

| Compound | Herbicidal effects | | | | |
|---|---|---|---|---|---|
| No. | Ec | Po | Am | Ch | Cy |
| 55 | 5 | 5 | 5 | 5 | 5 |
| 57 | 5 | 5 | 5 | 5 | 5 |
| 58 | 5 | 5 | 5 | 5 | 5 |
| 59 | 5 | 5 | 5 | 5 | 5 |
| 60 | 5 | 5 | 5 | 5 | 5 |
| 61 | 5 | 5 | 5 | 5 | 5 |
| 62 | 5 | 5 | 5 | 5 | 5 |
| 64 | 5 | 5 | 5 | 5 | 5 |
| 70 | 5 | 5 | 5 | 5 | 5 |
| 72 | 5 | 5 | 5 | 5 | 5 |
| 73 | 5 | 5 | 5 | 5 | 5 |
| 74 | 5 | 5 | 5 | 5 | 5 |
| 78 | 5 | 5 | 5 | 5 | 5 |
| 79 | 5 | 5 | 5 | 5 | 5 |
| 80 | 5 | 5 | 5 | 5 | 5 |
| 84 | 5 | 5 | 5 | 5 | 5 |
| 89 | 5 | 5 | 5 | 5 | 5 |
| 90 | 5 | 5 | 5 | 5 | 5 |
| 91 | 5 | 5 | 5 | 5 | 5 |
| 92 | 5 | 5 | 5 | 5 | 5 |
| 93 | 5 | 5 | 5 | 5 | 5 |
| 94 | 5 | 5 | 5 | 5 | 5 |
| 96 | 5 | 5 | 5 | 5 | 5 |
| 100 | 5 | 5 | 5 | 5 | 5 |
| 101 | 5 | 5 | 5 | 5 | 5 |
| 102 | 5 | 5 | 5 | 5 | 5 |
| 103 | 5 | 5 | 5 | 5 | 5 |
| 104 | 5 | 5 | 5 | 5 | 5 |
| 105 | 5 | 5 | 5 | 5 | 5 |
| 106 | 5 | 5 | 5 | 5 | 5 |
| 107 | 5 | 5 | 5 | 5 | 5 |

TABLE 6-continued

| Compound | Herbicidal effects | | | | |
|---|---|---|---|---|---|
| No. | Ec | Po | Am | Ch | Cy |
| 108 | 5 | 5 | 5 | 5 | 5 |
| 109 | 5 | 5 | 5 | 5 | 5 |
| 110 | 5 | 5 | 5 | 5 | 5 |
| 113 | 5 | 5 | 5 | 5 | 5 |
| 114 | 5 | 5 | 5 | 5 | 5 |

TEST EXAMPLE 4

Herbicidal and phytotoxicity tests in soil treatment of paddy field

Into a 1/5,000 a Wagner pot, paddy field soil was filled and puddled, and water was introduced thereto. In the pot, three germinated tubers of sagittaria (Sa) were embeded in the surface layer of the soil, and seeds of water plantain (Al) were sown. Further, two rice plants of 2.5 leaf stage were transplanted in a depth of 2 cm. Then, water was introduced to a depth of 3 cm. Next day, a prescribed amount of wettable powder formulated in accordance with Formulation Example 1, was diluted with water and dropwise applied to the water surface. Then, the pot was left in a green house, and 30 days after the application, the herbicidal effect and phytotoxicity were evaluated in accordance with the standards identified in Table 2. The results are shown in Tables 7 and 8.

TABLE 7

| Compound No. | Dose of active ingredients (gai/10a) | Herbicidal | | Phytotoxicity |
|---|---|---|---|---|
| | | Al | Sa | |
| 6 | 12.5 | 5 | 5 | 0 |
| 9 | 12.5 | 5 | 5 | 0 |
| 12 | 12.5 | 5 | 5 | 0 |
| 15 | 12.5 | 5 | 5 | 0 |
| Oxadiazon | 50 | 5 | 5 | 2.0 |
| | 25 | 5 | 2 | 2.0 |
| | 12.5 | 5 | 1 | 1.0 |

TABLE 8

| Compound No. | Dose of active ingredients (gai/10a) | Herbicidal | | Phytotoxicity |
|---|---|---|---|---|
| | | Al | Sa | |
| 55 | 25 | 5 | 5 | 0.5 |
| 60 | 12.5 | 5 | 5 | 0 |
| 70 | 25 | 5 | 5 | 0 |
| 71 | 25 | 5 | 5 | 0 |
| 72 | 25 | 5 | 5 | 0 |
| 76 | 12.5 | 5 | 5 | 0 |
| 80 | 25 | 5 | 5 | 0 |
| 88 | 12.5 | 5 | 5 | 0 |
| 96 | 25 | 5 | 5 | 0 |
| 98 | 25 | 5 | 5 | 0 |
| 104 | 25 | 5 | 5 | 0.5 |
| 112 | 25 | 5 | 5 | 0.5 |
| Oxadiazon | 12.5 | 4.5 | 1 | 1.5 |

TEST EXAMPLE 5

Selectivity test for soybean

Into a 120 $cm^2$ plastic pot, upland field soil was filled, and seeds of soybean (Gl), cocklebur (Xa) and morning-glory (Ip) were sown. After cultivating in a green house for 14 days, a prescribed amount of a wettable powder formulated in accordance with Formulation Example 1 was diluted with water in an amount of 100 liter/10 a and applied to the foliage of the plants from above by a small size spray. After the application, the pot was left in a green house for 21 days, and then the herbicidal effects and phytotoxicity were evaluated in accordance with the standards identified in Table 2. The results are shown in Tables 9 and 10.

In the table, symbol "-" means that the test was not conducted.

TABLE 9

| Compound No. | Dose of active ingredients (gai/10a) | Phytoto-xicity G l | Herbicidal X a | I p |
|---|---|---|---|---|
| 1 | 10 | 0 | 4.5 | — |
| 2 | 3 | 0.5 | 5 | 5 |
| 3 | 10 | 0 | 5 | 4 |
| 6 | 10 | 0 | 5 | — |
| 7 | 10 | 0 | 5 | 5 |
| 8 | 3 | 0 | 5 | 4.5 |
| 9 | 10 | 1 | 5 | 4.5 |
| 10 | 10 | 0 | 5 | 4.5 |
| 11 | 3 | 0.5 | 5 | 5 |
| 12 | 10 | 0 | 5 | — |
| 13 | 10 | 0 | 5 | — |
| 15 | 10 | 0.5 | 5 | — |
| 16 | 10 | 0 | 5 | — |
| Oxadiazon | 50 | 1 | 3 | 2 |
| | 25 | 0.5 | 2 | 1 |
| | 6.3 | 0 | 0 | 0.5 |

TABLE 10

| Compound No. | Dose of active ingredients (gai/10a) | Phytoto-xicity G l | Herbicidal X a | I p |
|---|---|---|---|---|
| 55 | 1.6 | 0 | 5 | 4.5 |
| 56 | 1.6 | 0.5 | 5 | 5 |
| 57 | 1.6 | 0 | 5 | 5 |
| 58 | 1.6 | 0 | 5 | 4.5 |
| 61 | 1.6 | 0.5 | 5 | 5 |
| 62 | 1.6 | 0.5 | 5 | 5 |
| 64 | 1.6 | 0 | 5 | 5 |
| 66 | 1.6 | 0.5 | 5 | 5 |
| 74 | 1.6 | 0 | 5 | 5 |
| 78 | 1.6 | 0.5 | 5 | 5 |
| 79 | 1.6 | 0 | 5 | — |
| 80 | 6.4 | 0 | 5 | 5 |
| 81 | 1.6 | 0.5 | 5 | 5 |
| 83 | 1.6 | 0 | 5 | — |
| 84 | 1.6 | 0 | 5 | 5 |
| 85 | 6.4 | 0 | 5 | 4.5 |
| 87 | 1.6 | 0 | 5 | 5 |
| 94 | 1.6 | 0.5 | 5 | 5 |
| 95 | 1.6 | 0.5 | 5 | 5 |
| 101 | 1.6 | 0.5 | 5 | 5 |
| 102 | 6.4 | 0 | 5 | 5 |
| 104 | 1.6 | 0.5 | 5 | 5 |
| 105 | 1.6 | 0.5 | 5 | 5 |
| 106 | 1.6 | 0 | 5 | 5 |
| 107 | 1.6 | 0.5 | 5 | 5 |
| Oxadiazon | 25 | 1 | 2.5 | 1 |

TEST EXAMPLE 6

Herbicidal and phytotoxicity tests in foliage treatment in upland field

Into a 330 $cm^2$ plastic pot, upland field soil was filled, and seeds of rice (Or), wheat (Tr), corn (Ze), slender amaranth (Am), lambsquarters (Ch) and velvetleaf (Ab) were sown and grown in a green house until the rice grew to the 3 leaf stage. When the rice reached the 3 leaf stage, a prescribed amount of a wettable powder formulated in accordance with Formulation Example 1 was diluted with water in an amount of 100 liter/10 a and applied to the foliage of the plants from above by a small size spray. After the application, the pot was left in a green house for 21 days, and then the herbicidal effects and phytotoxicity were evaluated in accordance with the standards identified in Table 2. The results are shown in Tables 11 and 12.

TABLE 11

| Compound No. | Dose of active ingredi-ents (gai/10a) | Phytotoxicity Or | Tr | Ze | Herbicidal Am | Che | Ab |
|---|---|---|---|---|---|---|---|
| 2 | 1.6 | 0.5 | 0 | 0 | 5 | 5 | 5 |
| 9 | 1.6 | 0 | 0 | 0 | 5 | 5 | 5 |
| 15 | 1.6 | 0 | 0.5 | 0 | 5 | 5 | 5 |
| Oxadiazon | 25 | 1 | 1.5 | 1.5 | 4.5 | 4.5 | 5 |
| | 6.3 | 1 | 0.5 | 1 | 2 | 3.5 | 4.5 |
| | 1.6 | 0 | 0 | 0 | 0.5 | 1 | 2.5 |

TABLE 12

| Compound No. | Dose of active ingred-ients (gai/10a) | Phytotoxicity Or | Tr | Ze | Herbicidal Am | Che | Ab |
|---|---|---|---|---|---|---|---|
| 55 | 1.6 | 0.5 | 0 | 0 | 5 | 5 | 5 |
| 57 | 1.6 | 0.5 | 0 | 0 | 5 | 5 | 5 |
| 58 | 0.4 | 0.5 | 0 | 0 | 5 | 5 | 5 |
| 83 | 1.6 | 0 | 0 | 0 | 5 | 5 | 5 |
| 84 | 0.4 | 0 | 0 | 0 | 5 | 5 | 5 |
| 88 | 1.6 | 0.5 | 0 | 0 | 5 | 5 | 5 |
| 92 | 0.4 | 0 | 0 | 0.5 | 5 | 5 | 5 |
| 93 | 1.6 | 0.5 | 0 | 0.5 | 5 | 5 | 5 |
| 94 | 0.4 | 0 | 0 | 0 | 5 | 5 | 5 |
| 95 | 1.6 | 0 | 0 | 0 | 5 | 5 | 5 |
| 96 | 0.4 | 0.5 | 0 | 0 | 5 | 5 | 5 |
| 98 | 0.4 | 0 | 0 | 0 | 5 | 5 | 5 |
| 99 | 0.4 | 0 | 0 | 0.5 | 5 | 5 | 5 |
| 101 | 1.6 | 0 | 0 | 0 | 5 | 5 | 5 |
| 106 | 0.4 | 0 | 0 | 0 | 5 | 5 | 5 |
| 109 | 0.4 | 0 | 0 | 0 | 5 | 5 | 5 |
| 110 | 0.4 | 0 | 0 | 0 | 5 | 5 | 5 |
| Oxadiazon | 6.3 | 1 | 1 | 1 | 2 | 3.5 | 4 |
| | 1.6 | 0 | 0 | 0 | 1 | 1.5 | 2 |

Among the compounds of the present invention, Compound Nos. 2, 7, 8, 10, 11, 20, 21, 26, 27, 28, 29, 32, 40, 41, 46, 52, 54, 57, 58, 60, 63, 84, 94, 95, 101 and 104 are preferred.

We claim:

1. A thiadiazabicyclononane derivative having the formula:

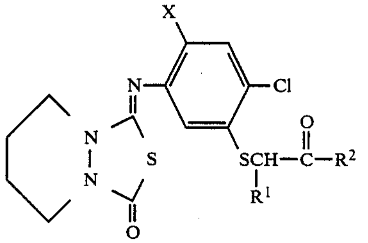

(I)

wherein X is hydrogen or halogen, $R^1$ is hydrogen or lower alkyl, $R^2$ is lower alkenyloxy, lower alkynyloxy, lower alkythio, halogen-substituted alkoxy lower alkosy, lower alkoxycarbonyl (lower) alkoxy α, α-dimethylbenzylamino, $—OC_2H_4S(O)_lR^3$ (wherein $R^3$ is alkyl or phenyl, and l is an integer of 0 or 2),

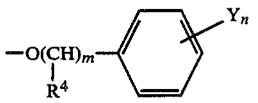

(wherein Y is halogen, lower alkyl, lower alkoxy or nitro, $R^4$ is hydrogen or lower alkyl, and each of m and n is an integer of 0, 1 or 2), $—OC_2H_4OR^5$ (wherein $R^5$ is phenyl, benzyl or methoxyalkyl), $—OCH_2R^6$ (wherein $R^6$ is styryl, cyanoalkyl, tetrahydrofuran-2-yl, thienyl or pyridin-2-yl),

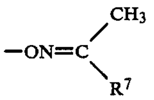

(wherein $R^7$ is lower alkyl or phenyl) or

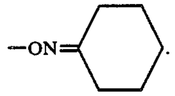

2. The thiadiazabicyclononane derivative according to claim 1, wherein $R^2$ is lower alkenyloxy, lower alkynyloxy, lower alkylthio, halogen-substituted lower alkoxy, lower alkoxycarbonyl (lower) alkoxy $—OC_2H_4S(O)_lR^{3'}$ (wherein $R^{3'}$ is lower alkyl, and l is an integer of 0 or 2) or

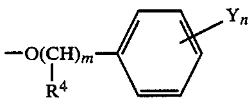

(wherein Y, $R^4$, m and n are as defined in claim 1).

3. The thiadiazabicyclononane derivative according to claim 1, wherein $R^2$ is lower alkynyloxy, halogen-substituted lower alkoxy, lower alkoxycarbonyl (lower) alkoxy

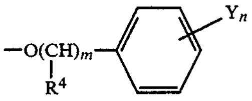

(wherein Y, $R^4$, m and n are as defined in claim 1), $—OC_2H_4OR^5$ (wherein $R^5$ is as defined in claim 1) or $—OCH_2R^6$ (wherein $R^6$ is as defined in claim 1).

4. The thiadiazabicyclononane derivative according to claim 1, wherein $R^2$ is lower alkynyloxy, halogen-substituted lower alkoxy, lower alkoxycarbonyl (lower) alkoxy

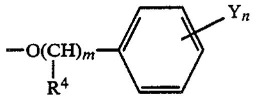

(wherein Y, $R^4$, m and n are as defined in claim 1).

5. The thiadiazabicyclononane derivative according to claim 1, wherein $R^2$ is

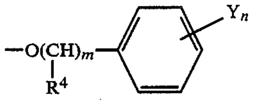

(wherein Y, $R^4$, m and n are as defined in claim 1).

6. The thiadiazabicyclononane derivative according to claim 1, wherein $R^2$ is $—OC_2H_4OR^5$ (wherein $R^5$ is as defined in claim 1), or $—OCH_2R^6$ (wherein $R^6$ is as defined in claim 7. The thiadiazabicyclononane derivative according to claim 1, wherein $R^2$ is

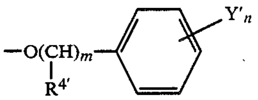

(wherein Y' is halogen, $R^{4'}$ is hydrogen or methyl and each of m and n is an integer of 0, 1 or 2).

8. The thiadiazabicyclononane derivative according to claim 1, wherein $R^2$ is

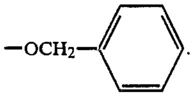

9. The thiadiazabicyclononane derivative according to claim 1, wherein $R^1$ is hydrogen.

10. The thiadiazabicyclononane derivative according to claim 8, wherein $R^1$ is hydrogen.

11. The thiadiazabicyclononane derivative according to claim 1, wherein X is hydrogen or fluorine.

12. A herbicidal composition comprising a herbicidally effective amount of a compound of the formula I as defined in claim 1 and an agriculturally acceptable carrier.

* * * * *